(12) United States Patent
Anno

(10) Patent No.: US 7,438,870 B2
(45) Date of Patent: *Oct. 21, 2008

(54) AIR CLEANER

(76) Inventor: Koji Anno, 23-13 Matsubara 3-chome, Setagaya-ku, Tokyo (JP) 156-0043

( * ) Notice: Subject to any disclaimer, the term of this patent is extended or adjusted under 35 U.S.C. 154(b) by 964 days.

This patent is subject to a terminal disclaimer.

(21) Appl. No.: 10/816,884

(22) Filed: Apr. 5, 2004

(65) Prior Publication Data

US 2004/0184975 A1    Sep. 23, 2004

Related U.S. Application Data

(63) Continuation of application No. 10/019,290, filed as application No. PCT/JP00/04442 on Jul. 4, 2000, now Pat. No. 6,843,969.

(30) Foreign Application Priority Data

Jul. 5, 1999   (JP)   ................. 11-190817
Feb. 8, 2000   (JP)   ................. 2000-030900

(51) Int. Cl.
    *B01J 19/08*    (2006.01)
(52) U.S. Cl. ............... 422/186.04; 422/186.07; 422/121; 96/97
(58) Field of Classification Search ............ 422/186.04, 422/186.07, 121; 96/97
    See application file for complete search history.

(56) References Cited

U.S. PATENT DOCUMENTS

| | | | |
|---|---|---|---|
| 2,354,817 A | 8/1944 | Law | |
| 2,732,501 A | 1/1956 | Blaeker | |
| 5,535,089 A | 7/1996 | Ford et al. | |
| 5,601,636 A | 2/1997 | Glucksman | |
| 5,814,135 A | 9/1998 | Weinberg | |
| 5,847,514 A | 12/1998 | Dai et al. | |
| 6,843,969 B1 * | 1/2005 | Anno | ............ 422/186.04 |

FOREIGN PATENT DOCUMENTS

| | | |
|---|---|---|
| EP | 0 278 653 | 8/1988 |
| EP | 0 637 859 A1 | 2/1995 |
| GB | 2 313 995 | 12/1997 |
| JP | 109836/1982 | 7/1982 |
| JP | 61-215201 | 9/1986 |
| JP | 180041/1986 | 11/1986 |
| JP | 7-308373 | 11/1995 |
| KR | 20-0149487 | 3/1999 |

* cited by examiner

*Primary Examiner*—Kishor Mayekar
(74) *Attorney, Agent, or Firm*—Oblon, Spivak, McClelland, Maier & Neustadt, P.C.

(57) ABSTRACT

An air cleaning device includes a bulb-shaped casing provided at one end with an attached portion to be attached an attaching portion and connected to a commercial power source and at the other end with an outlet, an ozone generator accommodated in the casing and an air supply portion formed in the casing for supplying air into the ozone generator. The ozone generator includes a needle first electrode having a distal end directed to the outlet and a cylindrical second electrode concentric with the first and second electrodes. Application of high voltage between the first and second electrodes induces electrical discharge therebetween, generates negative ions and ozone and releases a stream of air containing the generated negative ions and ozone from the first electrode to the second electrode and outlet.

9 Claims, 14 Drawing Sheets

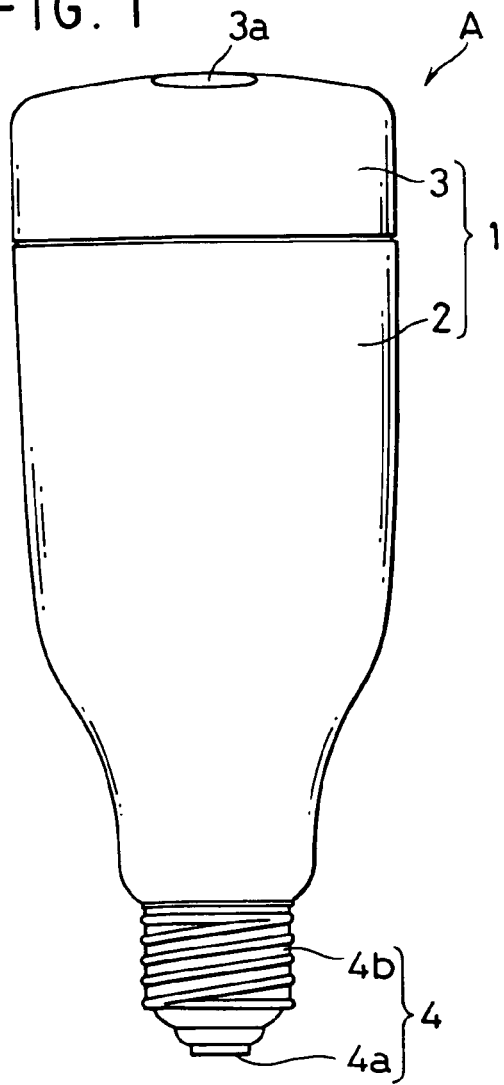
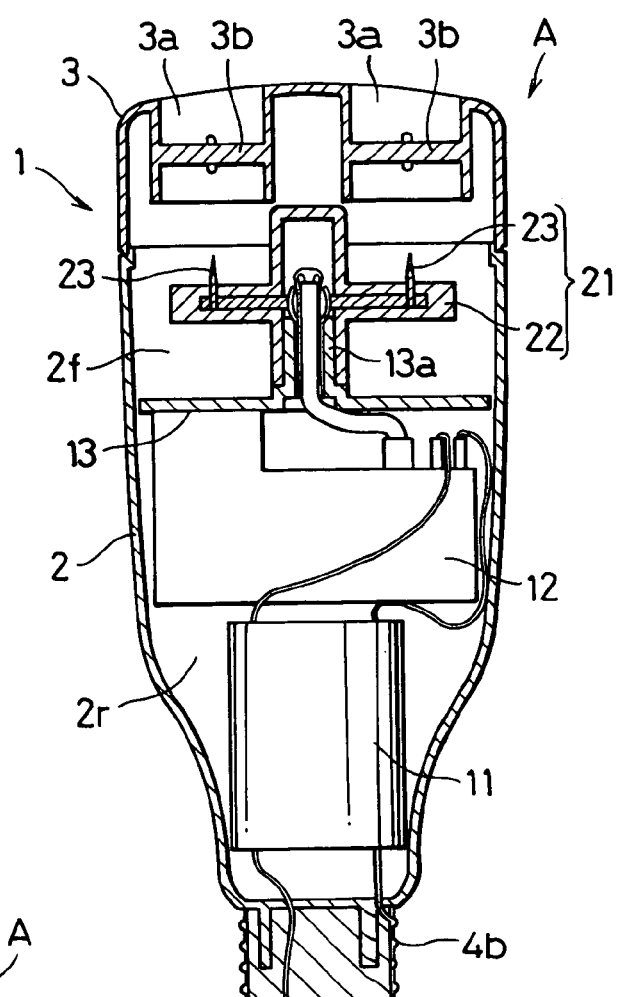
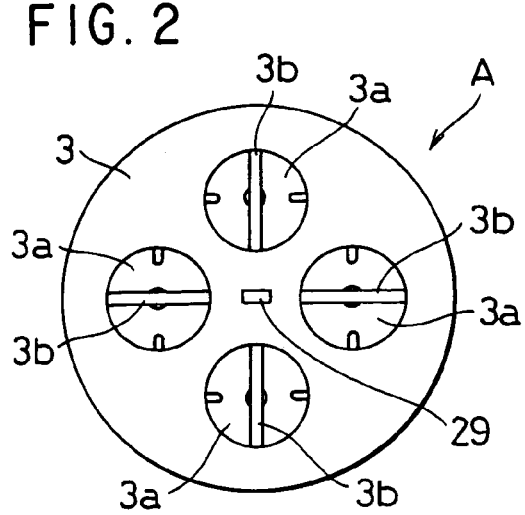

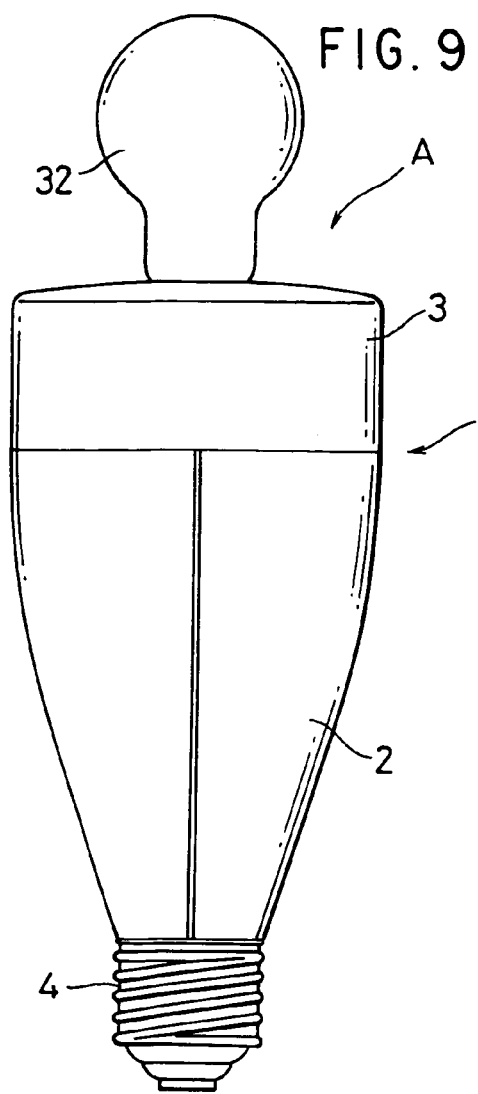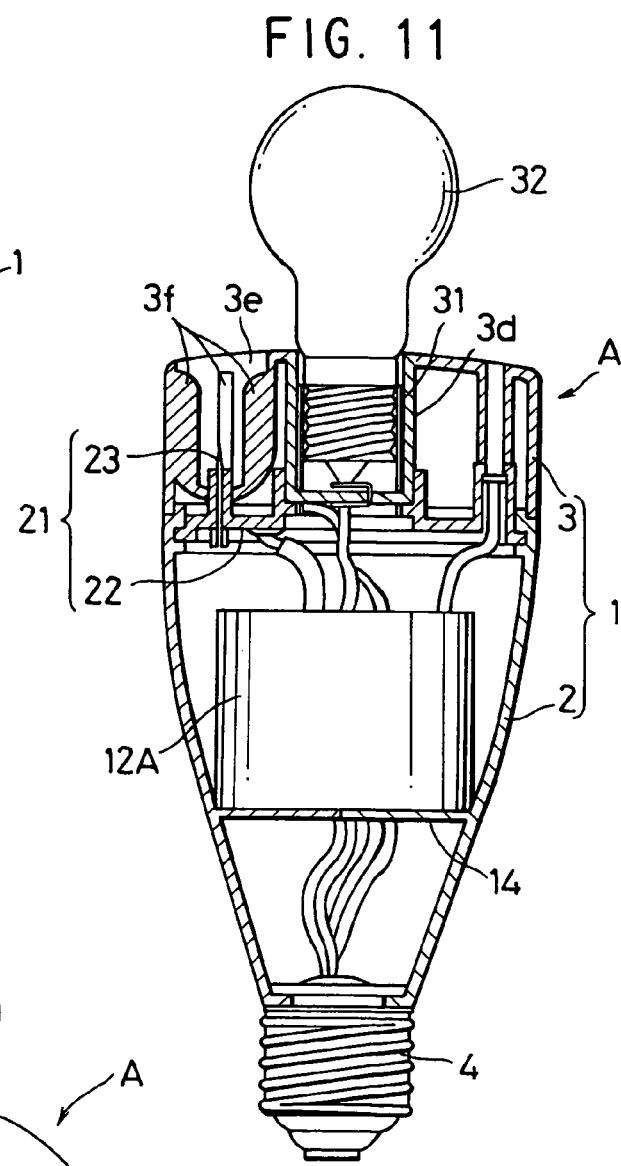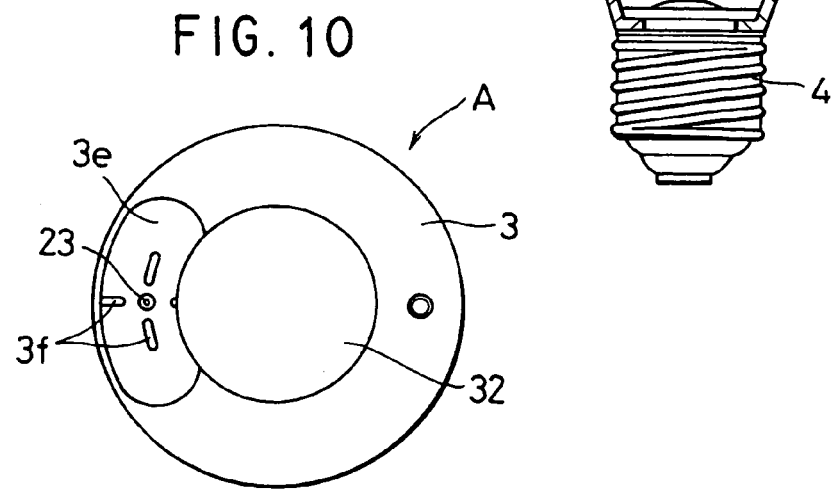

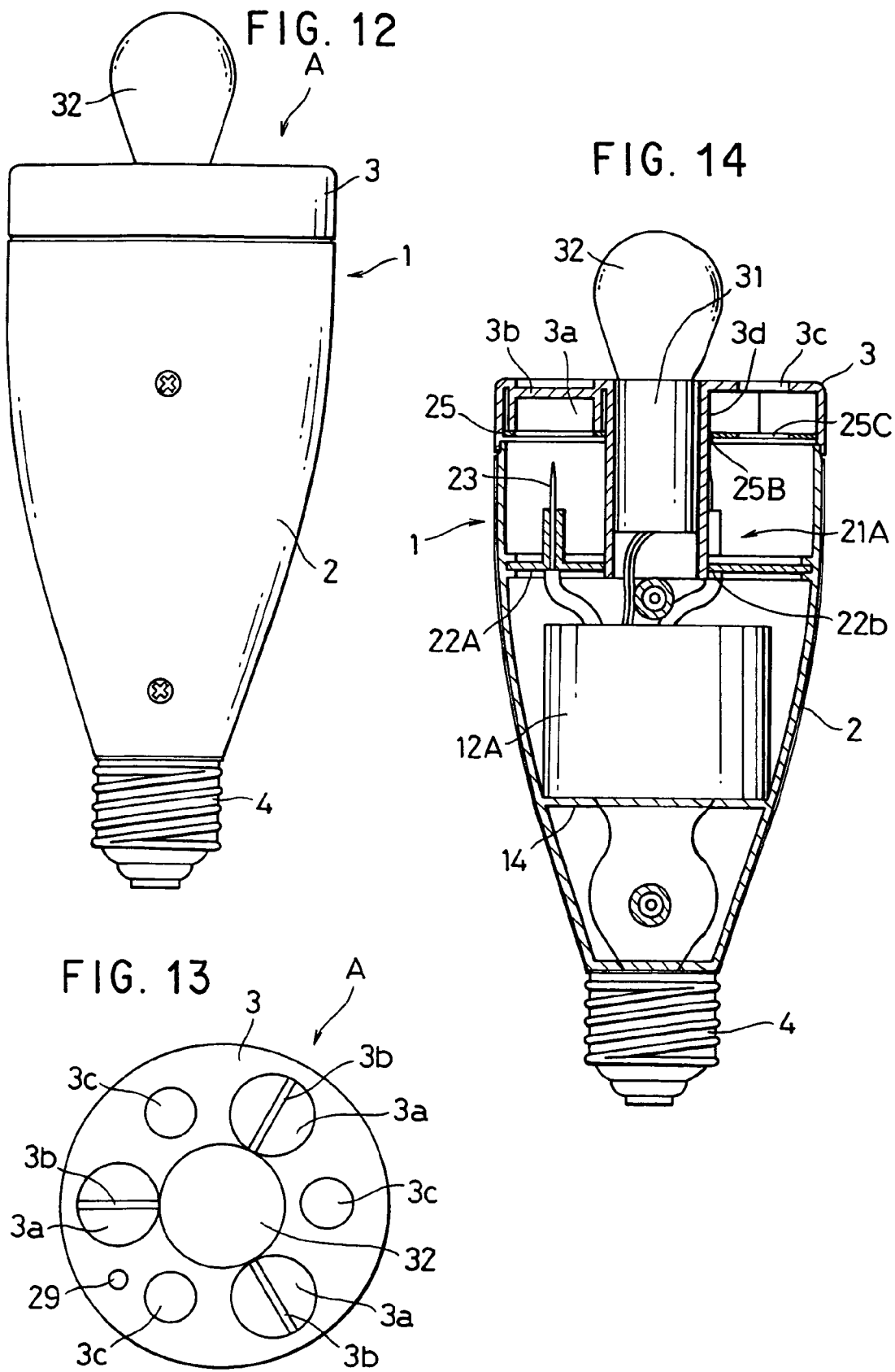

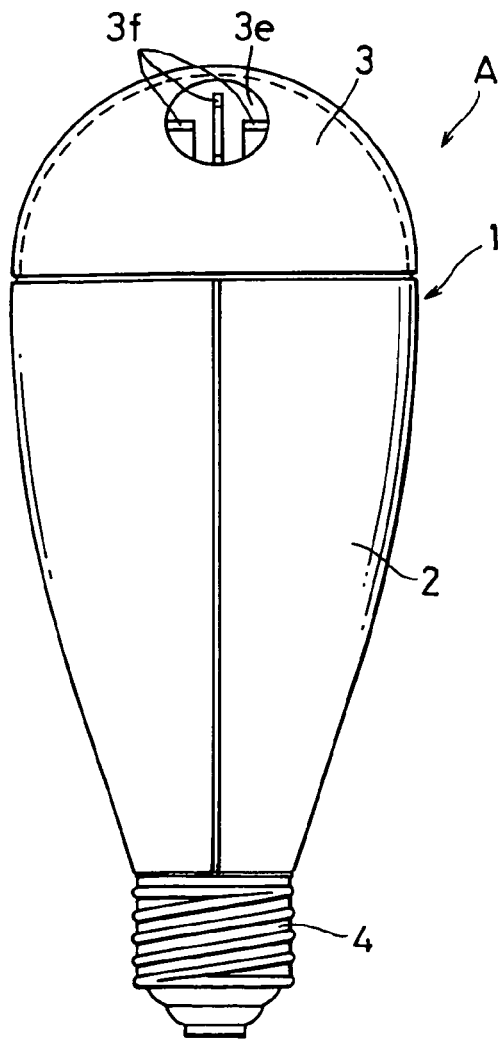
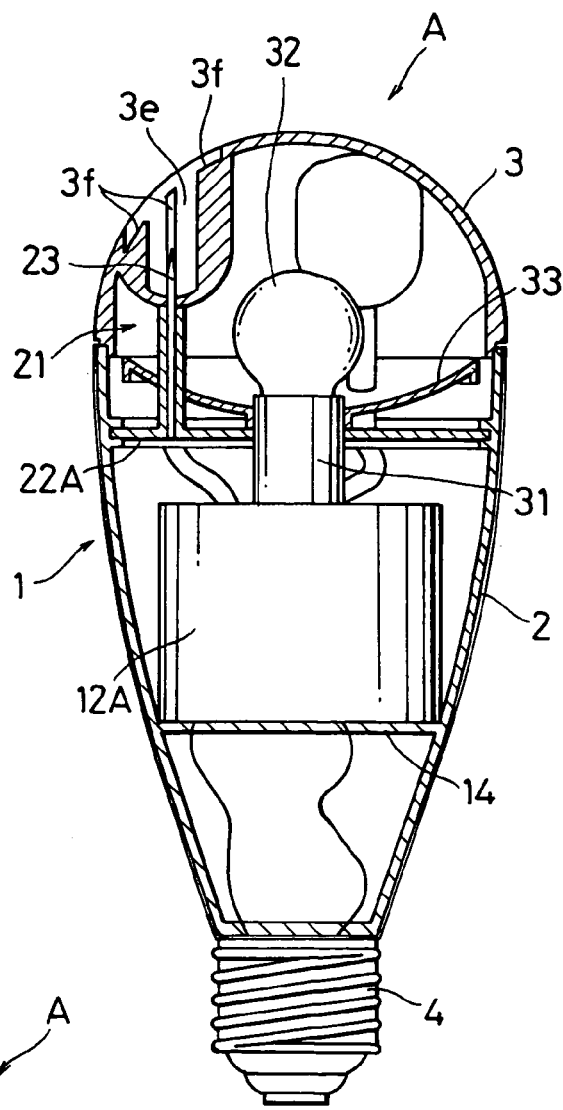
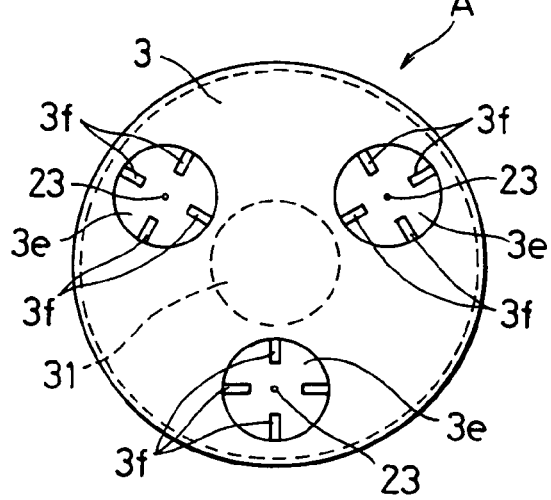

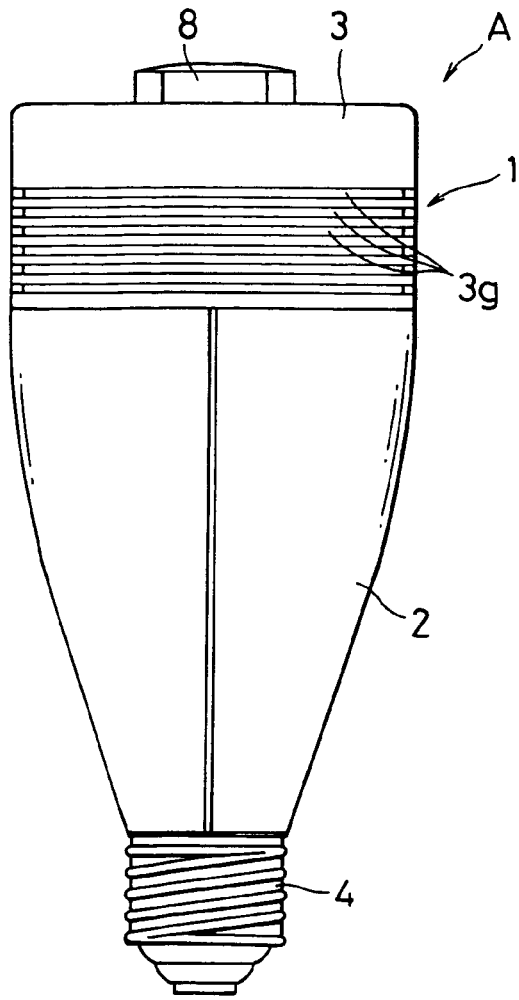
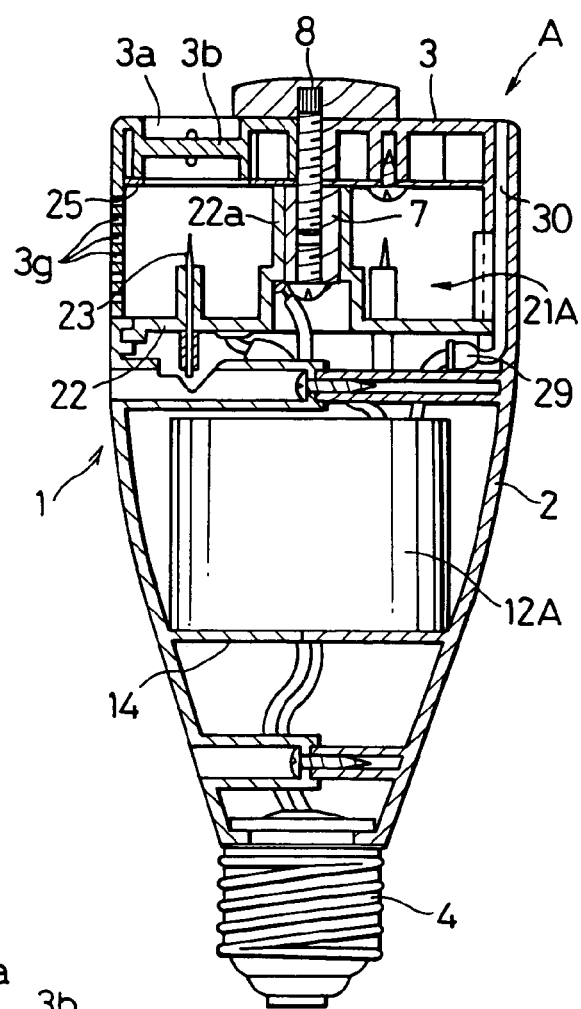
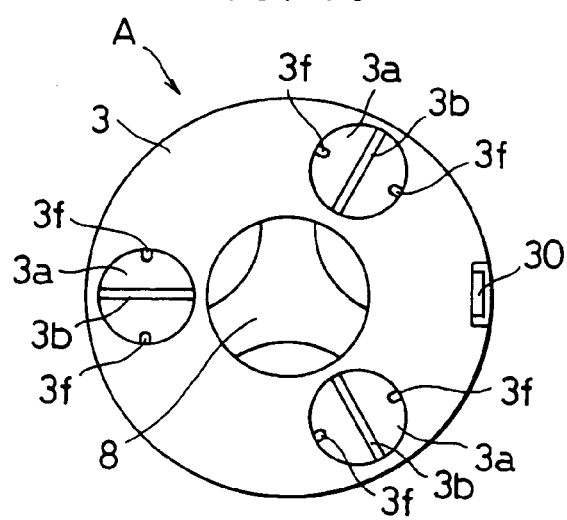

AIR CLEANER

CROSS-REFERENCE TO RELATED APPLICATIONS

This application is a continuation of U.S. patent application Ser. No. 10/019,290, filed Jan. 4, 2002, now U.S. Pat. No. 6,843,969, which is a National Stage Application of PCT Application No. PCT/JP00/04442, filed Jul. 4, 2000, the entire contents of each of which are incorporated herein by reference.

FIELD OF ART

This invention relates to an air cleaning device that generates and diffuses negative ions known to have a "forest bathing effect" and ozone having bactericidal and deodorant actions and that is equipped with lighting.

BACKGROUND ART

Conventional air cleaning devices are used by inserting a plug attached to a power cord into an electrical receptacle and set in position within a house or automobile.

Since the conventional air cleaning devices are of the mount-type as described above, it is impossible to release and diffuse negative ions alone or both negative ions and ozone from above a room or compartment and its mounting location is restricted to some extent.

This invention has been accomplished to eliminate the above inconvenience. One object of the invention is to provide an air cleaning device that can be used in any mode by attaching an attached portion (a fed portion) to an attaching portion (a feed portion) without restricting its mounting location.

DISCLOSURE OF THE INVENTION

An air cleaning device according to this invention comprises a bulb-shaped casing provided at one end with an attached portion to be attached to an attaching portion and at the other end with an outlet, and a negative ion generator accommodated within the casing, whereby negative ions are generated by electric discharge of the negative ion generator and released from the outlet.

Another aspect of this invention provides an air cleaning device comprising a bulb-shaped casing provided at one end with a fed portion to be attached to a feed portion and at the other end with an outlet, an AC/DC converter accommodated in the casing for converting an alternating current from the fed portion into a direct current, a boosting transformer accommodated in the casing for boosting the voltage from the AC/DC converter, and a negative ion generator accommodated in the casing so as to face the outlet and connected to the boosting transformer, whereby negative ions are generated by electric discharge resulting from application of high voltage from the boosting transformer to the negative ion generator and are released from the outlet.

The negative ion generator in the above air cleaning device comprises a needle-like electrode having its distal end directed toward the outlet.

Still another aspect of this invention provides an air cleaning device comprising a bulb-shaped casing that accommodates an ozone generator therein, has its one end provided with an attached portion to be attached to an attaching portion and its opposite end provided with an outlet, and is equipped with an air supply portion for supplying air to the ozone generator, whereby negative ions and ozone are generated by electric discharge of the ozone generator to produce a stream of air containing the negative ions and ozone and flowing from the ozone generator to the outlet.

Yet another aspect of this invention provides an air cleaning device comprising a bulb-shaped casing provided at one end with a fed portion to be attached to a feed portion and at the other end with an outlet, an AC/DC converter accommodated in the casing for converting an alternating current from the fed portion into a direct current, a boosting transformer accommodated in the casing for boosting the voltage from the fed portion, an ozone generator accommodated in the casing so as to face the outlet and connected to the boosting transformer, and an air supply portion for supplying air to the ozone generator in the casing, whereby negative ions and ozone are generated by electric discharge resulting from application of high voltage from the boosting transformer to the ozone generator to produce a stream of air containing the negative ions and ozone and flowing from the ozone generator to the outlet.

The bulb-shaped casing may comprise a casing body having one end provided with the fed portion and an opposite open end, and a lid having one end provided with the outlet and the opposite end firmly or detachably attached to the open end of the casing body.

The ozone generator may comprise a first needle-like electrode connected to the negative pole of the boosting transformer and having a distal end directed to the outlet, and a second electrode in the form of a cylinder concentric with the first electrode or a plate with a circular opening concentric with the first electrode, the first electrode being accommodated in the casing body and the second electrode being positioned concentrically relative to the outlet and accommodated in the lid.

In any of the air cleaning devices, the AC/DC converter and boosting transformer may be made integral; the opposite end of the casing may be provided with lighting; and the feed portion may comprise a base to be attached to or detached from a socket, a base equipped with a pair of pins projecting from the periphery at opposed locations, or a plug equipped with a pair of blades or pins to be inserted into or pulled out from an electrical receptacle.

Since the casing of the air cleaning device is formed in the shape of an electric bulb and provided at one end with the fed portion or attached portion and at the other end with the outlet, electric power from a socket for an illuminator, a socket built in the ceiling or roof, or an electrical receptacle for a reading lamp can be used as the power source for the air cleaning device. Therefore, the air cleaning device can be disposed on the floor, suspended from above, hung on the wall or set in position at an optional location so that negative ions alone or both negative ions and ozone can be released in an optional direction to obtain a forest bathing effect and clean, sterilize and deodorize the interior of a room or compartment.

BRIEF DESCRIPTION OF THE DRAWINGS

FIG. 1 a front view showing a first embodiment of an air cleaning device according to this invention.

FIG. 2 is a plan view of the air cleaning device shown in FIG. 1.

FIG. 3 is a longitudinal cross section of the air cleaning device shown in FIG. 1.

FIG. 9 is a front view showing a fifth embodiment of the air cleaning device according to this invention.

FIG. 10 is a plan view of the air cleaning device shown in FIG. 9.

FIG. 11 is a longitudinal cross section of the air cleaning device shown in FIG. 9.

FIG. 12 is a front view showing a sixth embodiment of the air cleaning device according to this invention.

FIG. 13 is a plan view of the air cleaning device shown in FIG. 12.

FIG. 14 is a longitudinal cross section of the air cleaning device shown in FIG. 12.

FIG. 15 is a front view showing a seventh embodiment of the air cleaning device according to this invention.

FIG. 16 is a plan view of the air cleaning device shown in FIG. 15.

FIG. 17 is a longitudinal cross section of the air cleaning device shown in FIG. 15.

FIG. 18 is a front view showing an eighth embodiment of the air cleaning device according to this invention.

FIG. 19 is a plan view of the air cleaning device shown in FIG. 18.

FIG. 20 is a longitudinal cross section of the air cleaning device shown in FIG. 18.

FIG. 21($b$) is a bottom view of the air cleaning device shown in FIG. 21($a$).

FIG. 22($b$) is a bottom view of the air cleaning device shown in FIG. 22($a$).

FIG. 23($b$) is a bottom view of the air cleaning device shown in FIG. 23($a$).

FIG. 24($b$) is a bottom view of the air cleaning device shown in FIG. 24($a$).

FIG. 29($b$) is an explanatory view illustrating the attachment of FIG. 29($a$) inserted into an electrical receptacle.

BEST MODE FOR WORKING THE INVENTION

Figure 4:
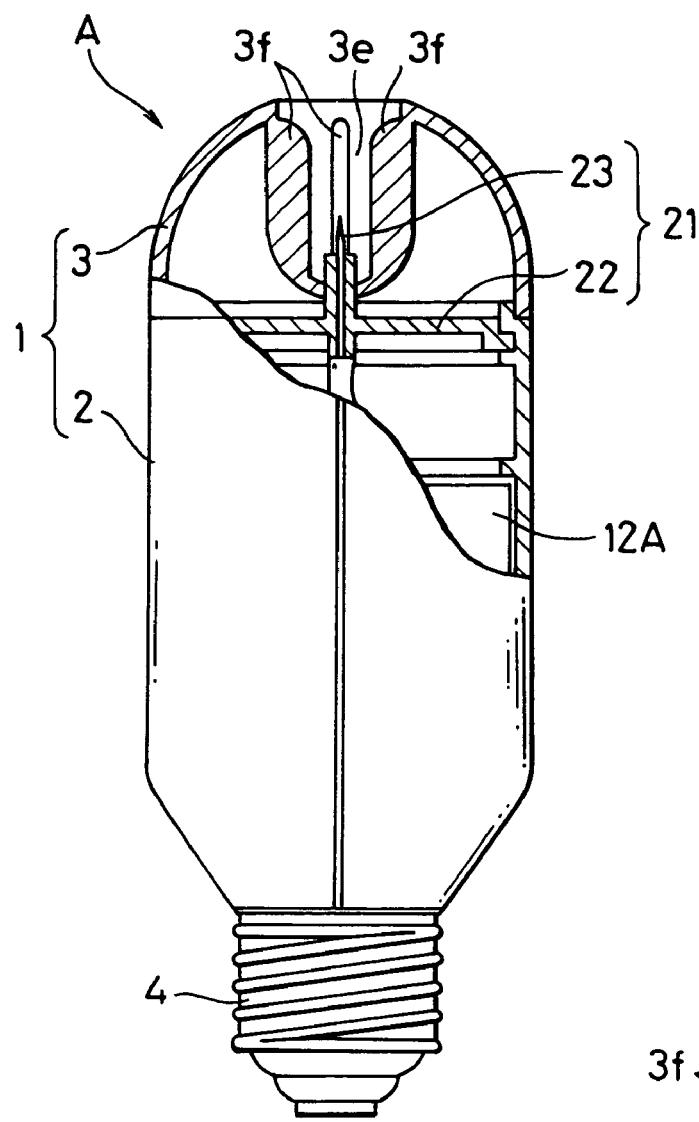
FIG. 4 is a front view, partially sectioned, showing a second embodiment of the air cleaning device according to this invention.

The present invention will be described in detail below with reference to the accompanying drawings.

FIG. 1 is a front view illustrating a first embodiment of an air cleaning device A according to this invention, FIG. 2 a plan view illustrating the air cleaning device of FIG. 1, and FIG. 3 a longitudinal cross section illustrating the air cleaning device of FIG. 1, with its part sectioned.

In these figures, denoted by reference numeral 1 is a bulb-shaped casing that comprises a casing body 2 of synthetic resin and a lid 3 of synthetic resin having at its distal end a spherical surface of large curvature approximating to a flat plane.

One end of the casing body 2 of the casing 1 is open and the other end thereof is provided with a base (a fed portion) 4 attached to a socket (a feed portion), not shown, to form connection with a commercial power source.

The distal end surface of the lid 3 corresponding to the distal end of the casing 1 is provided with plural, e.g. four, cylindrical outlets 3$a$ of the same diameter that are arranged along a circle concentric with the distal end surface.

The lid 3 has a structure detachably attached by fitting or by other such means to the open end of the casing body 2 and is provided with cross pieces 3$b$ for preventing the fingers etc. from being inserted into the outlets 3$a$ to serve as safety means.

The base 4, like the base of an ordinary electric bulb, has at its one end center one electrode 4$a$ and at its periphery the other electrode 4$b$.

The inside of the casing body 2 is divided into a front side chamber 2$f$ and a back side chamber 2$r$ accommodating an AC/DC converter 11 and a boosting transformer 12 by a partition wall 13 that serves also as a mounting member. The partition wall 13 is provided with a round cylindrical support 13$a$ positioned at the center of the four outlets 3$a$ of the lid 3 and projecting toward the front side chamber 2$f$. The partition wall 13 is desirably made of an insulating material. The AC/DC converter 11 accommodated in the back side chamber 2$r$ converts an alternating current from the base 4 into a direct current that is output into the boosting transformer 12 which is accommodated in the back side chamber and in which the input direct current is boosted.

Within the front side chamber 2$f$ is accommodated a negative ion generator 21 that comprises an insulating support base 22 equipped with a cylindrical portion attached onto the cylindrical support 13$a$ of the partition wall 13 and four needle-like conductive first electrodes 23 arranged along a circle concentric with the support base 22, with their respective distal ends directed toward the centers of the four outlets 3$a$ of the lid 3. The four first electrodes 23 are collectively connected to the negative pole side of the boosting transformer 12.

The distal end surface of the lid 3 is provided at the center with a light emitting diode 29 that displays the operation or non-operation state of the negative ion generator 21.

The casing body 2 and lid 3 are configured such that when they are made integral by relative movement and fitting, each first electrode 23 is positioned at the center of the outlet 3$a$ by positioning means, e.g. concave and convex means, provided respectively on the casing body 2 and lid 3.

The operation of the air cleaning device A constructed as described above will be described.

By applying negative high DC voltage to the first electrodes 23 from the boosting transformer 12, silent corona discharge is induced between the distal end of each first electrode and the atmosphere forward of each first electrode to generate negative ions. The negative ions pass through a corresponding outlet 3a from each first electrode 23 side and are released by the Coulomb force of the charged atmosphere forward of each first electrode 23.

Since negative ions are generated from the first electrode 23 side inward of the outlets 3a, they are diffused into a room in which the air cleaning device A is disposed to clean the air in the room.

The light emitting diode 29 turns on a light during the operation of the negative ion generator 21 to indicate the generation of negative ions.

However, when a switch or other such means is used to stop the operation of the negative ion generator 21, the light emitting diode 29 puts out lights to indicate non-generation of negative ions.

The principle of negative ions cleaning the air is that negative ions are attached to positive ions (dust on the order of microns, dead ticks, mold, bacteria, pollen, etc.) thought to be harmful to the human body to convert the positive ions into negative ions heavier than the air, that fall on the floor and are adsorbed onto the floor made positive.

The positive ions converted into negative ions and falling on the floor are removed by a vacuum cleaner.

From the first electrode 23, not less than one-million negative ions per milliliter are released all the time. In order to obtain a larger effect, it is desirable to increase the number of the first electrode 23 to release a greater number of negative ions.

While negative ions are thought to have a "forest bathing effect", they act to relax mind and body, prevent oxidization of cells, activate metabolism, heighten the functions of the lugs and the respiratory organ system, and enhance internal secretion to improve the hematogenic action.

These functions of negative ions are proved by the test date using an AMI (Apparatus for measuring the function of the Meridians and their corresponding Internal organs), according to which the blood flow of patients in the atmosphere of negative ions artificially generated is activated and the flow of their internal animation is made good.

According to the first embodiment, as described above, since the casing 1 is bulb-shaped and provided with the base 4 attachable directly to a socket, when it is attached to an illuminator socket or other such socket, it is possible to diffuse negative ions from above in a room etc. to clean the air in the room etc.

In addition, since the bulb-shaped casing 1 is of a suspendible type, it is possible to provide a novel air cleaning device with various applications, as compared with conventional mount-type air cleaning devices disposed on the floor, a desk or other such flat place.

Furthermore, the provision of the cross pieces 3b in the outlets 3a can prevent the fingers from being inserted into the outlets 3a and getting in touch with the first electrode 23. Thus, safety can be ensured.

Moreover, since the casing 1 is divided into the casing body 2 and the lid 3 that are detachably attached, the interior of the lid 2 after being detached from the casing body 2 can be simply cleaned and washed with ease.

The air cleaning device A in the first embodiment has no electrode facing the first electrode 23 to induce electric discharge between the first electrode 23 and the ambient air. This will not dirty the inside of the casing 1 and less require cleaning and washing of the inside of the casing 1, thus making the device maintenance easy.

Since the inside of the casing 1 is less liable to dirty as described above, the lid 3 and the casing body 2 can be fixed to or made integral with each other.

The provision of the light-emitting diode 29 that can turn on a light and put out lights enables the user to confirm whether or not the air cleaning device A releases negative ions.

Figure 5:
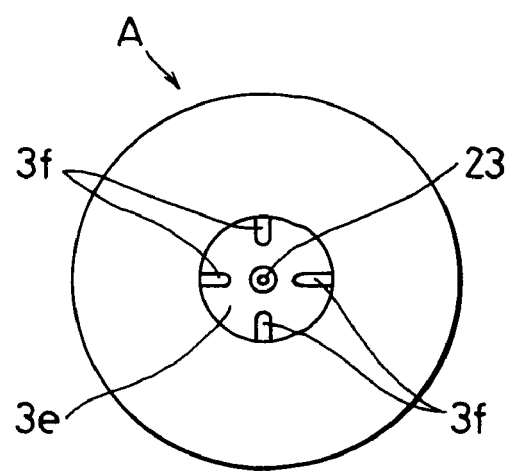
FIG. 5 is a plan view of the air cleaning device shown in FIG. 4.

FIG. 4 is a front view, partially sectioned, showing a second embodiment of the air cleaning device according to this invention, and FIG. 5 is a plan view of the air cleaning device shown in FIG. 4. In this embodiment, the same reference numerals as in FIGS. 1 to 3 are given to the identical or corresponding elements, the explanation of which will be omitted from the following description.

While the air cleaning device according to the first embodiment is provided with a plurality of negative ion generators, the air cleaning device in this embodiment is equipped with a single negative ion generator. A semicircular lid 3 has a center recess 3e serving as the outlet. A support base 22 is provided at the center with a first electrode 23 that pierces through the bottom of the recess 3e to constitute a negative ion generator 21 in conjunction with the support base 22. The wall of the lid 3 defining the recess 3e is provided with four ribs 3f disposed at 90-degree intervals so as to surround the first electrode 23, thereby serving as safety means. Furthermore, in this embodiment, an AC/DC converter is integral with a boosting transformer 12A in a built-in manner.

In the same manner as in the first embodiment, application of negative high DC voltage from the boosting transformer 12A to the first electrode 23 induces silent corona discharge to generate negative ions that are released from the center recess 3e of the lid 3.

In this embodiment, since there is a single negative ion generator and further since the AC/DC converter is built in the boosting transformer, the air cleaning device can be made compact.

Figure 6:
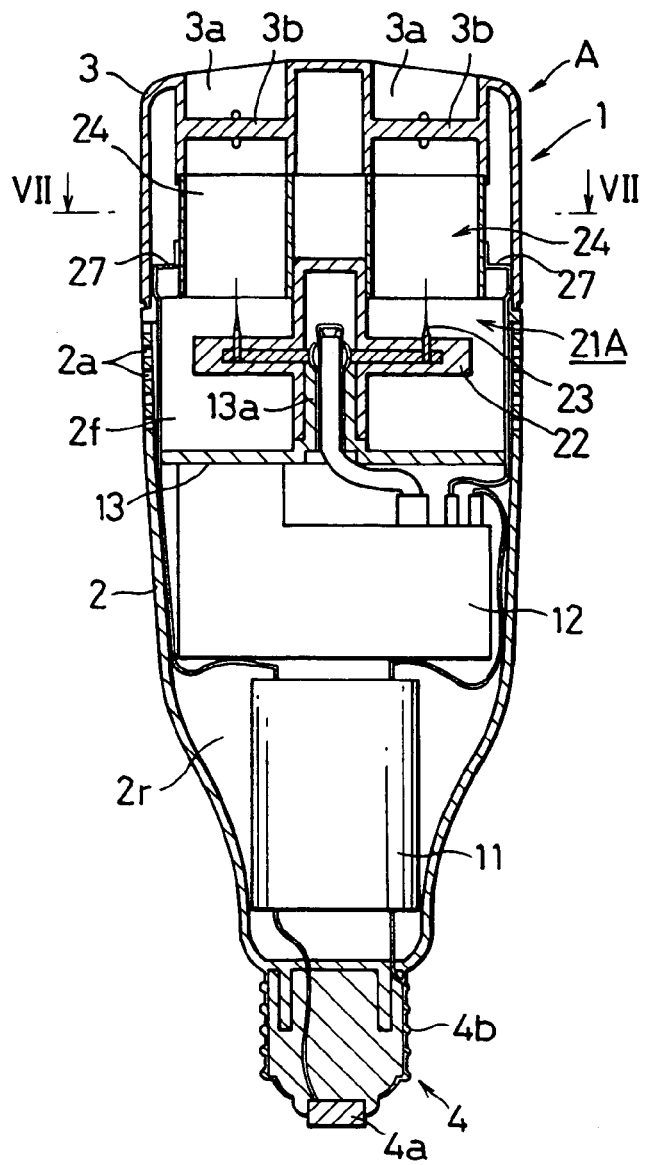
FIG. 6 is a longitudinal cross section showing a third embodiment of the air cleaning device according to this invention.
Figure 7:
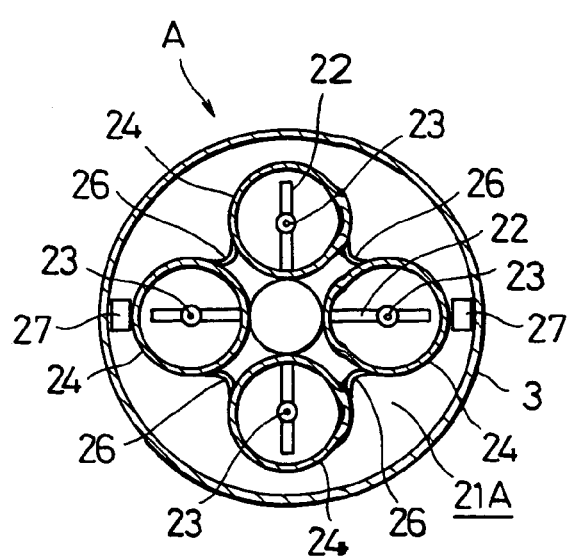
FIG. 7 is a cross section taken along line VII-VII in FIG. 6.

FIG. 6 is a longitudinal cross section showing a third embodiment of the air cleaning device according to this invention, and FIG. 7 is a cross section taken along line VII-VII in FIG. 6. In this embodiment, the same reference numerals as in FIGS. 1 to 3 are given to the identical or corresponding elements, the explanation of which will be omitted from the following description.

In FIGS. 6 and 7, a casing body 2 is provided in the peripheral wall on its open (distal end) side with slitted openings 2a circumferentially disposed at predetermined intervals and communicating with its front side chamber 2f to serve as portions for supplying air into an ozone generator 21A which will be described later.

Within the inside portion of a lid 3 on the open side of the casing body 2 are accommodated four cylindrical second conductive electrodes 24 each concentric with an outlet 3a. One end of each second conductive electrode 24 is fitted in and supported by the outlet 3a, and each distal end of needle-like first electrodes 23 supported on a support base 22 in the front side chamber 2f of the casing body 2 enters the opposite open end of each second electrode 24. The first electrodes 23, second electrodes 24 and support base 22 constitute the aforementioned ozone generator 21A.

The inside portion of the lid 3 on the open side of the casing body 2 is provided with two conductive retainers 27 disposed at predetermined positions at an interval of 180 degrees, for example, so that the conductive retainers 27 come into pressure contact with and support opposed second electrodes 24 and, when the lid 3 is attached to the casing body 2, function as contactors electrically connecting the opposed second electrodes 24 respectively via conductors to the positive poles of an AC/DC converter 11 and a boosting transformer 12. In addition, adjacent second electrodes 24 are electrically connected to each other via a conductive connector 26.

Furthermore, a light emitting diode (not shown) is disposed at an appropriate position to display the operation state of the ozone generator 21A.

The operation of the air cleaning device A in this embodiment will be described.

When a high DC voltage is applied between the first electrodes 23 serving as the negative poles and the second electrodes 24 serving as the positive poles, silent corona discharge is induced between the distal end of each first electrode 23 and a portion of each second electrode 24 nearest to the distal end of each first electrode 23 to generate negative ions and ozone. The Coulomb force of the electrified second electrodes 24 causes a stream of air containing negative ions and ozone to pass from the side of each first electrode 23 through each outlet 3a via each second electrode 24.

Air for successively inducing a stream of air passing from the side of each first electrode 23 through each outlet 3a via each second electrode 24 is supplied via the slitted openings 2a.

A stream of air containing negative ions and ozone passes from the side of each second electrode 24 through each outlet 3a and is released and diffused into a room. Thus, the air in the room in which the air cleaning device A is provided can be cleaned as described above and, at the same time, sterilization and deodorization can be attained by a small amount of ozone (not more than 0.05 ppm).

During the operation, dust is electrified and attached to the cylindrical second electrodes 24 to dirty the cylindrical second electrodes. The dirty second electrodes 24 are cleaned and washed after detaching the lid 3 from the casing body 2 or further detaching the second electrodes from the lid 3 that has been detached from the casing body 2. After this cleaning and washing, the lid 3 is attached to the casing body 2 or the second electrodes 24 are attached to the lid 3 and then the lid 3 is attached to the casing body 2.

The light emitting diode not shown turns on a light during the operation of the ozone generator 21A to indicate the generation of negative ions and ozone.

However, when a switch or other such means is used to stop the operation of the ozone generator 21A, the light emitting diode puts out lights to indicate non-generation of negative ions and ozone.

In the air cleaning device of this embodiment in particular, since the first electrodes 23 and the same number of cylindrical second electrodes 24 are disposed face to face respectively and also since needle-like electrodes are used as the first electrodes, negative ions and ozone can be generated efficiently and, at the same time, the cylindrical second electrodes 24 enable a stable velocity of an air stream and can increase the amount of the air stream.

Furthermore, since the lid 3 is detachable from and attachable to the casing body 2, the second electrodes 24 can be simply and easily cleaned and washed after detaching the lid 3 from the casing body 2 or after further detaching the second electrodes 24 from the lid 3.

Figure 8:
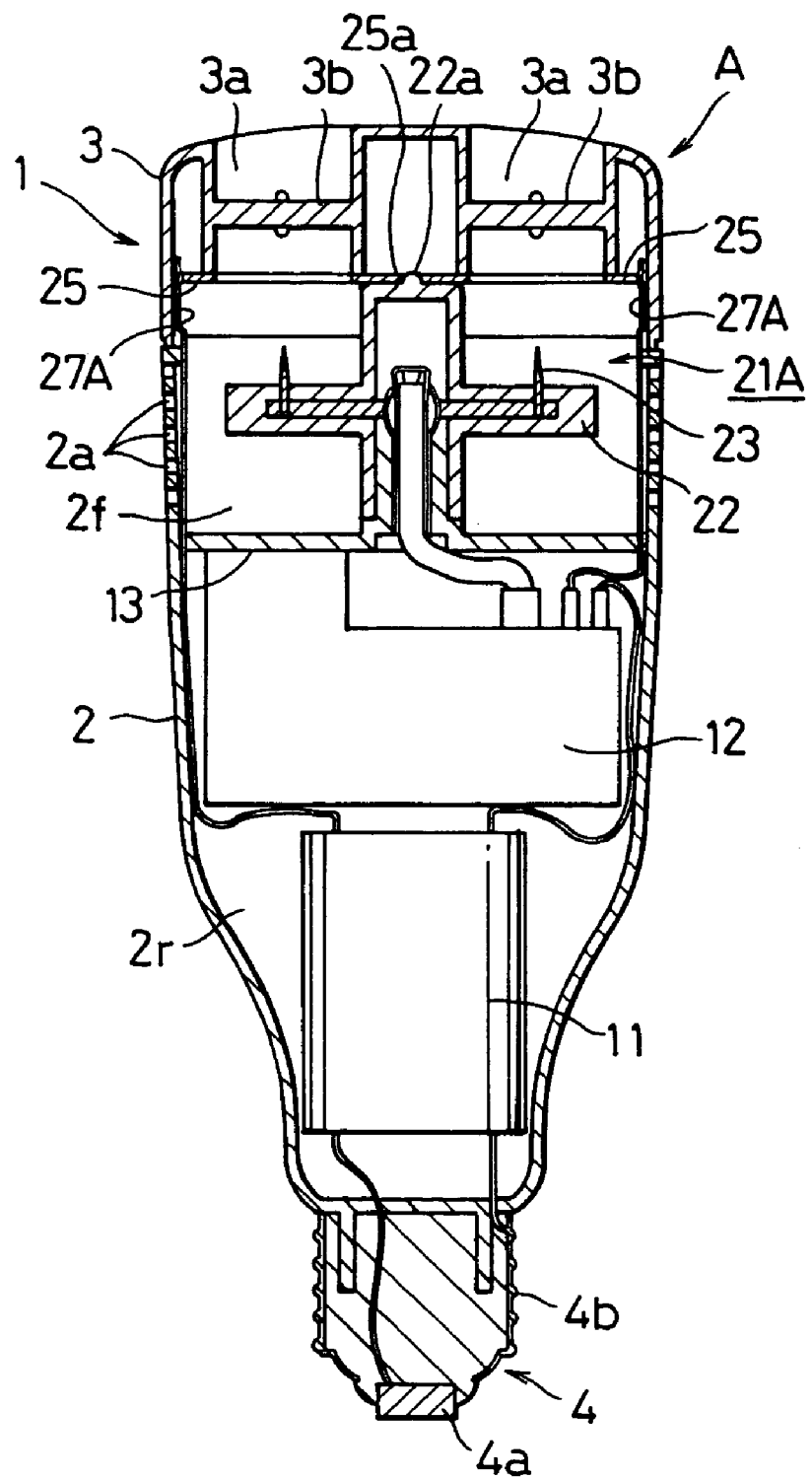
FIG. 8 is a longitudinal cross section showing a fourth embodiment of the air cleaning device according to this invention.

FIG. 8 is a longitudinal cross section showing a fourth embodiment of the air cleaning device according to this invention. In this embodiment, the same reference numerals as in FIGS. 1 to 7 are given to the identical or corresponding elements, the explanation of which will be omitted from the following description.

In FIG. 8, four platelike second electrodes 25 each having a circular opening are accommodated in a lid 3 in such a manner as being fixed or detachably attached to the portion of the lid 3 on the open side of a casing body and being concentric with and facing each first electrode 23. A positioning projection 22a provided on the center of the distal end of a support base 22 is adapted to engage with a center space 25a surrounded by the four second electrodes 25.

Therefore, when the positioning projection 22a has been engaged with the center space, the four first electrodes 23 are positioned at locations corresponding to the centers of the circular openings of the second electrodes.

The four first electrodes 23, four second electrodes 25 and support base 22 constitute an ozone generator 21A.

At predetermined positions of the outer peripheral edge of the second electrodes 25 at an interval of 180 degrees, for example, are provided conductive connectors 27A that function to position the second electrodes 25 inside the lid 3 and, when the lid 3 is attached to the casing body 2, function to electrically connect the second electrodes to the positive poles of an AC/DC converter 11 and a boosting transformer 12 via conductors.

A light emitting diode (29) not shown is provided on the casing body 2 or lid 3 at an appropriate position to indicate the operation state of the ozone generator 21A.

The difference between the operation of the air cleaning device A in this embodiment and that of the third embodiment device will be described.

When a high DC voltage is applied between the first electrodes 23 serving as the negative poles and the second electrodes 25 serving as the positive poles, silent corona discharge is induced between the distal end of each first electrode 23 and the circular opening edge of each second electrode 25 to generate negative ions and ozone. The Coulomb force of the electrified second electrodes 25 causes a stream of air containing negative ions and ozone to pass from the side of each first electrode 23 through each outlet 3a via each second electrode 25 and to be diffused.

During the operation, dust is electrified and attached to the second electrodes 25 to dirty the second electrodes 25. The dirty second electrodes 25 are cleaned and washed after detaching the lid 3 from the casing body 2 or further detaching the second electrodes from the lid 3 that has been detached from the casing body 2. After this cleaning and washing, the lid 3 is attached to the casing body 2 or the second electrodes 24 are attached to the lid 3 and then the lid 3 is attached to the casing body 2.

In the fourth embodiment, therefore, the same effects as in the third embodiment can be obtained.

FIG. 9 is a front view showing a fifth embodiment of the air cleaning device according to this invention, FIG. 10 is a plan view of the air cleaning device shown in FIG. 9, and FIG. 11 is a longitudinal cross section of the air cleaning device shown in FIG. 9. In this embodiment, the same reference numerals as in FIGS. 1 to 8 are given to the identical or corresponding elements, the explanation of which will be omitted from the following description.

As shown in these figures, a lid 3 of a bulb-shaped casing 1 is provided at the center an open cylindrical portion 3d equipped therein with a socket 31 that is electrically connected to a base 4 and to and from which an electric bulb 32 is attachable and detachable.

Outside of the cylindrical portion 3d a recess 3e serving as an outlet is formed. The distal end of a first electrode 23 supported on a support base 22 projects from the bottom of the recess. On the inner surface of the recess 3e four ribs 3f are formed so as to surround the first electrode 23, thereby protecting the first electrode.

Inside of a casing body 2 partitioned by the support base 22, there is formed a mounting wall 14 on which a boosting transformer 12A having an AC/DC converter integrally incorporated therein is supported. The boosting transformer 12A is electrically connected to the first electrode 23.

The operation of the air cleaning device A will be described. When high DC voltage is applied to the first electrode 23, negative ions are generated and released. The same effects as in the first and second embodiments can thus be obtained.

Since the air cleaning device A is equipped with illuminating means, by attaching the device to a socket for an electric bulb, the effects of negative ions can be obtained without necessitating provision of an illuminator.

FIG. 12 is a front view showing a sixth embodiment of the air cleaning device according to this invention, FIG. 13 is a plan view of the air cleaning device shown in FIG. 12, and FIG. 14 is a longitudinal cross section of the air cleaning device shown in FIG. 12. In this embodiment, the same reference numerals as in FIGS. 1 to 11 are given to the identical or corresponding elements, the explanation of which will be omitted from the following description.

As shown in these figures, a lid 3 is provided in its distal end surface with three outlets 3a and three openings 3c each formed between the adjacent outlets and on a circle passing through the centers of the outlets 3a, that have a function to supply air into an ozone generator 21A.

A safety measure is taken, if necessary, by providing the openings 3 with cross pieces similar to those 3b of the outlets 3a.

The lid is further provided at the center of its distal end surface with a cylindrical portion 3d extending into the open end side of a casing body 2, the outer periphery of which positions a second electrode 25 and the inside of which is formed with a socket 31 to and from which an electric bulb is attachable and detachable.

The casing body 2 is formed therein on its open end side with a partitioning support base 22A on which first electrodes 23 having their respective distal ends directed to the centers of the outlets 3a are arranged along a circle concentric with the open end of the casing body. The center of the support base is formed with a positioning hole 22b in which the cylindrical portion 3d of the lid 3 is fitted.

At the lower inside of the casing body 2 partitioned by the support base 22A, there is formed a mounting wall 14 on which a boosting transformer 12A having an AC/DC converter integrally incorporated therein is supported.

The platelike second electrode 25 having three circular holes is formed at its center with a positioning hole 25B in which the cylindrical portion 3d of the lid 3 is fitted and further with three circular holes 25C that are disposed between the adjacent holes and along a circle connecting the centers of the holes and face the three openings 3c. The air entering the lid 3 from the openings 3c is supplied from the holes 25C into the ozone generator 21A constituted of the first electrodes 23, second electrode 25 and partitioning support base 22A.

When the lid 3 has been attached to the casing body 2, the first electrodes 23, holes of the second electrode 25 and outlets 3a are disposed concentrically. The openings 3c and holes 25C are also disposed concentrically.

The second electrode 25 is connected to the positive pole of the boosting transformer 12A though this connection is not shown.

The difference between the operation of the air cleaning device A in this embodiment and that of the preceding embodiment devices will be described. When high DC voltage is applied between the first electrodes 23 and the second electrode 25 to generate negative ions and ozone, a stream of air containing the negative ions and ozone passes through the holes of the second electrode 25 and outlets 3a and is released.

Air for successively generating an air stream that passes from the side of the first electrodes 23 through the holes of the second electrode 25 and outlets 3a is supplied via the openings 3c and holes 25C.

The inside of a room can be illuminated as occasion demands by the electric bulb 32.

In the sixth embodiment, the same effects as in the third and fourth embodiments can be obtained. Since the air cleaning device in this embodiment is equipped with illuminating means, by attaching the device to a socket for an electric bulb, the effects of negative ions can be obtained without necessitating provision of an illuminator. Air cleaning can thus be attained.

FIG. 15 is a front view showing a seventh embodiment of the air cleaning device according to this invention, FIG. 16 is a plan view of the air cleaning device shown in FIG. 15, and FIG. 17 is a longitudinal cross section of the air cleaning device shown in FIG. 15. In this embodiment, the same reference numerals as in FIGS. 1 to 14 are given to the identical or corresponding elements, the explanation of which will be omitted from the following description.

In these figures, a lid 3 is made from transparent or translucent resin and provided in its distal end portion with three recesses 3e that are disposed on a circle and serve as outlets. When the lid has been attached to a casing body 2, three first electrodes 23 formed on a partitioning support base 22A have their respective distal ends projecting from the bottoms of the recesses 3e. Inside of each recess 3e, there are four ribs 3f disposed at intervals of 90 degrees to surround the first electrode 23 and function as safety means.

Above the partitioning support base 22A is provided a reflector 33 that is attached to a socket 31 for effectively reflecting light from an electric bulb 32.

While the operation of the air cleaning device A in this embodiment is substantially the same as that of the preceding embodiment, since the electric bulb 32 is covered by the lid 3, it is possible to eliminate direct contact with the electric bulb 32 and obtain soft indirect illuminating light through the lid 3.

FIG. 18 is a front view showing an eighth embodiment of the air cleaning device according to this invention, FIG. 19 is a plan view of the air cleaning device shown in FIG. 18, and FIG. 20 is a longitudinal cross section of the air cleaning device shown in FIG. 18. In this embodiment, the same reference numerals as in FIGS. 1 to 17 are given to the identical or corresponding elements, the explanation of which will be omitted from the following description.

In these figures, a lid 3 has slitted openings 3g formed circumferentially in its peripheral surface at regular intervals for supplying air into an ozone generator 21A.

A conductive internally threaded cylinder 7 is fitted in a cylindrical support portion 22a of a support base 22 disposed at the center of the open end of a casing body 2. The lid 3 is detachably attached to the casing body 2 by a fitting screw 8 having an insulating head and a shaft piercing through the lid 3 and helically engaging with the internally threaded cylinder 7.

A light guide plate 30 is provided between the casing body 2 and the lid 3 for guiding light from a light emitting diode 29 provided in the casing body 2 to the distal end side of the lid for emission.

A platelike second electrode 25 having circular holes is attached by the fitting screw to the lid 3 so that it is disposed concentrically with a circle connecting outlets 3a and a circle connecting first electrodes 23, and is electrically connected to a boosting transformer 12A integrally incorporating a AC/DC converter therein via the internally threaded cylinder 7, fitting screw attached to the internally threaded cylinder 7, etc.

While the operation of the air cleaning device A in this embodiment is substantially the same as that of the preceding embodiment, the device operation state in this embodiment can be confirmed from light guided by the light guide plate 30.

The fed portion of the air cleaning device according to the present invention will be described.

Figure 21:
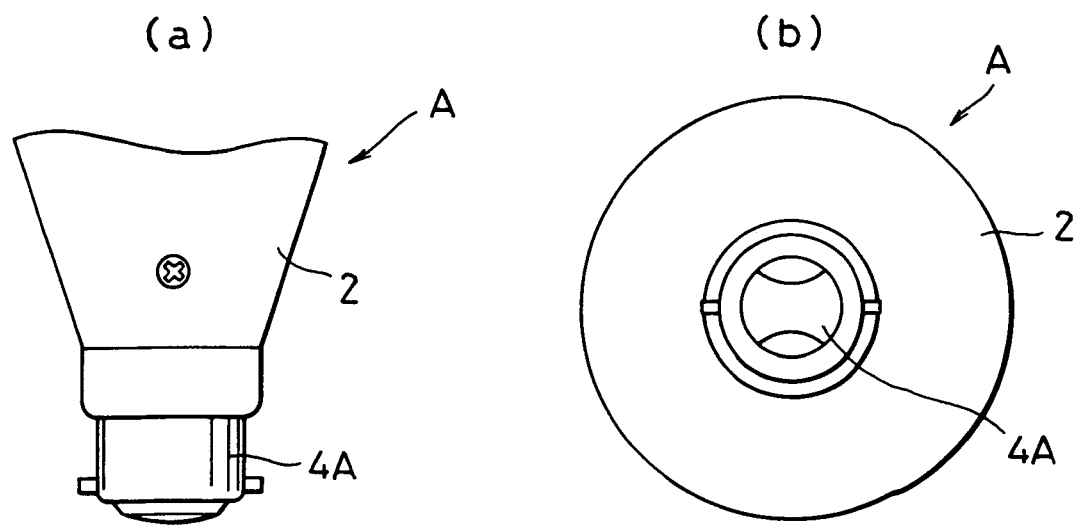
FIG. 21($a$) is a partial side view of an air cleaning device showing another example of a fed portion.
Figure 22:
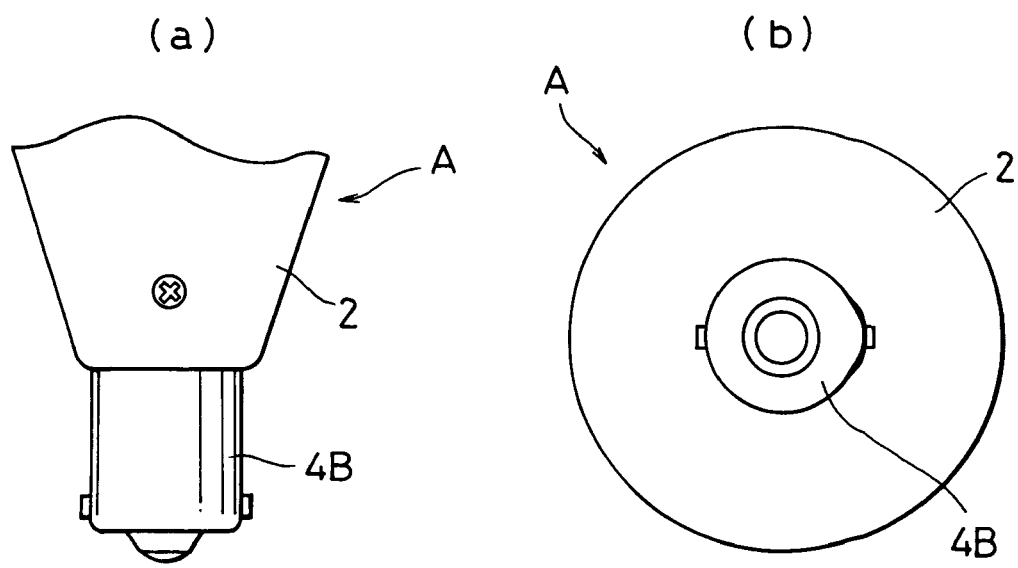
FIG. 22($a$) is a partial side view of an air cleaning device showing still another example of the fed portion.

While the base 4 for an ordinary electric bulb is used as the fed portion in the embodiments described so far, it can be changed to a base 4A of a so-called D-type as shown in FIGS. 21(a) and 21(b) in which a pair of slender pins project from the opposed positions of the periphery or a so-called S-type as shown in FIGS. 22(a) and 22(b) in which a pair of bold short pins project from the opposed positions of the periphery, depending on a corresponding electrical receptacle.

Figure 23:
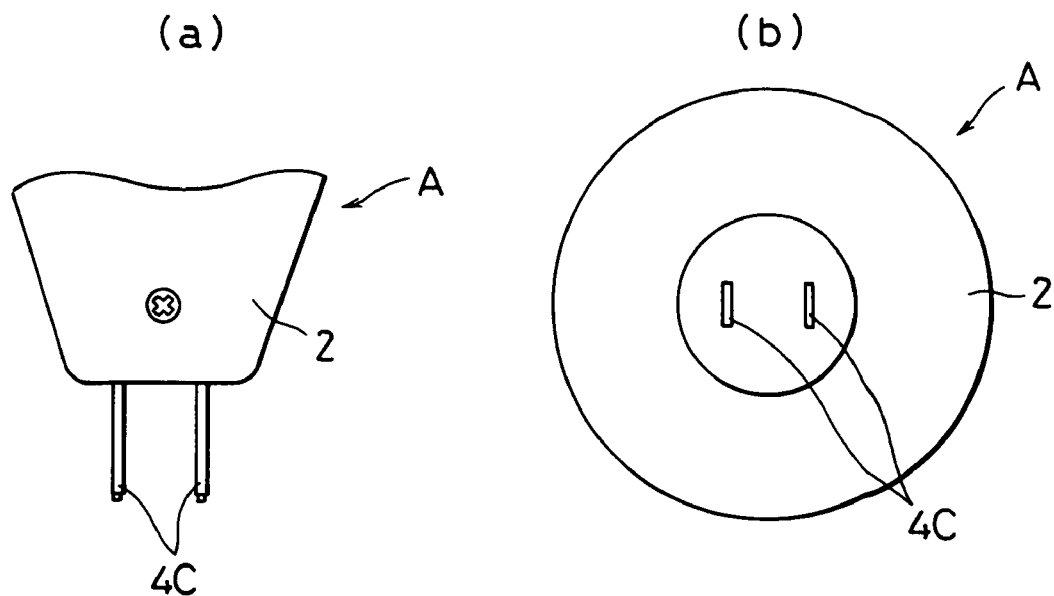
FIG. 23($a$) is a partial side view of an air cleaning device showing yet another example of the fed portion.
Figure 24:
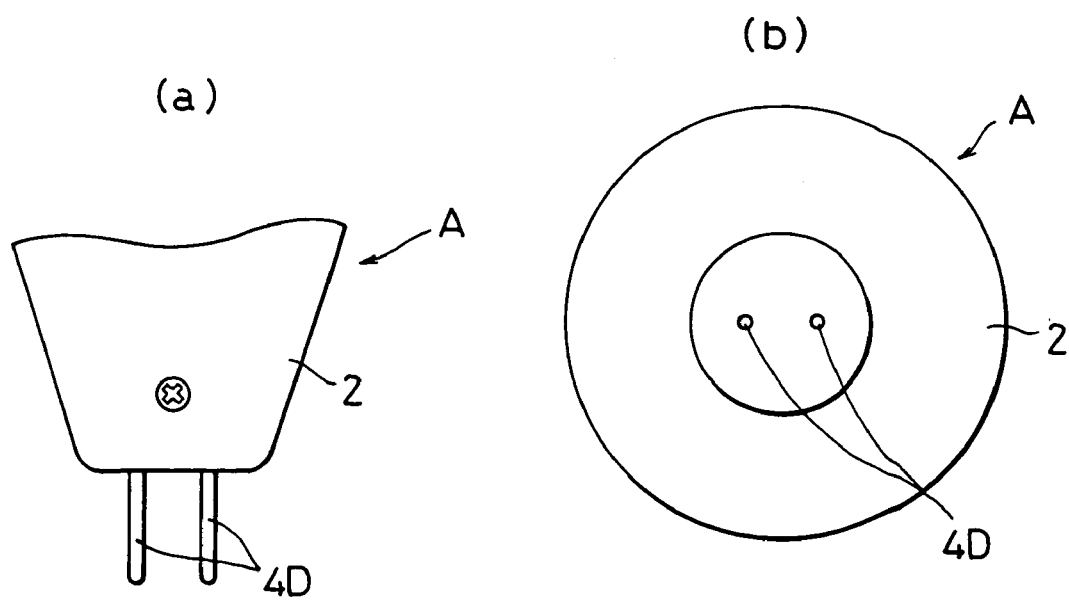
FIG. 24($a$) is a partial side view of an air cleaning device showing a further example of the fed portion.

Further, depending on a corresponding electrical receptacle, a plug having a pair of parallel blades 4C projecting from its one end as shown in FIGS. 23(a) and 23(b) or a plug having a pair of parallel pins 4D projecting from its one end as shown in FIGS. 24(a) and 24(b) can also be used as the fed portion.

Examples of attachment of the air cleaning device according to the present invention will be described.

Figure 25:
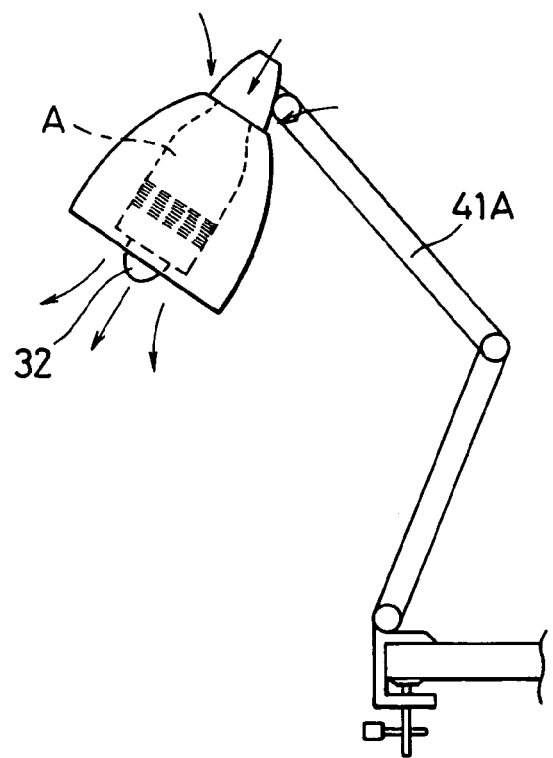
FIG. 25 is an explanatory view illustrating an air cleaning device according to this invention applied to a reading lamp supported on a movable arm having one end fixed to a wall or desk.
Figure 26:
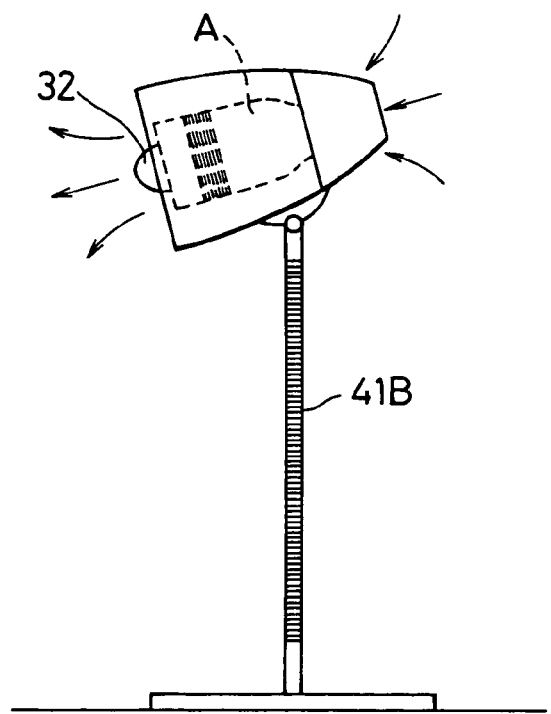
FIG. 26 is an explanatory view illustrating an air cleaning device according to this invention applied to a mount-type reading lamp.

FIG. 25 shows an example in which the air cleaning device A of this invention equipped with an illuminator 32 is attached to the socket of a reading lamp 41A supported on one end of a movable arm having the opposite end fixed to a desk or wall. FIG. 26 shows an example in which the air cleaning device A of this invention equipped with an illuminator 32 is attached to the socket of a mount-type reading lamp 41B. In these examples, the reading lamps can be used in the same manner as usual and, when a power switch is turned on, a flow of air containing negative ions or both negative ions and ozone is released from backward to forward of the lampshade, thereby relaxing mind and body and cleaning air.

Figure 27:
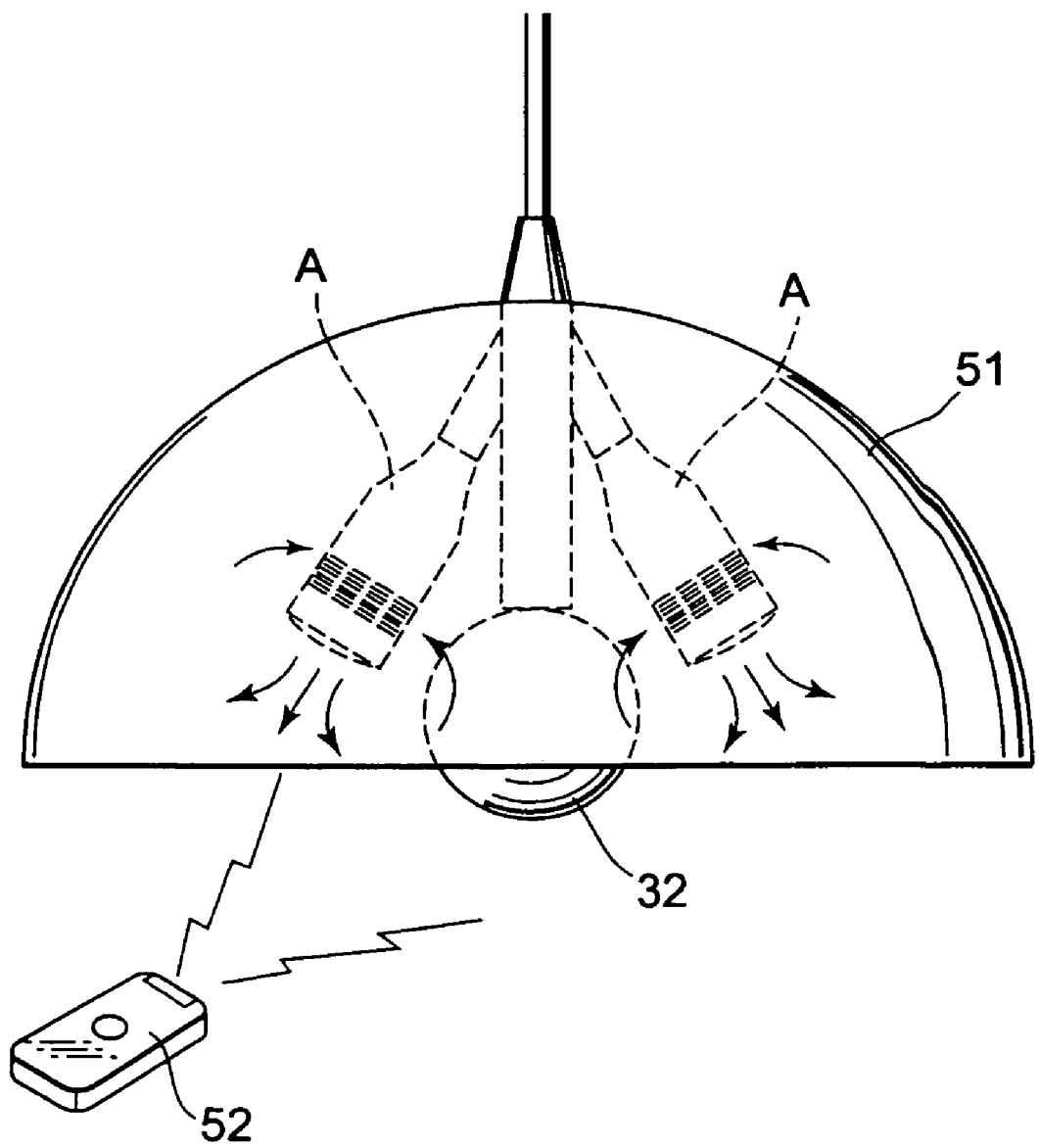
FIG. 27 is an explanatory view illustrating an air cleaning device according to this invention applied to an illuminator provided with a plurality of sockets.

FIG. 27 shows an example in which the air cleaning devices A of this invention are attached to vacant sockets of an illuminating implement 51 equipped with a plurality of sockets. When a remote controller 52 is used to turn the power switch on, a stream of air containing negative ions and ozone is released downward of the lampshade.

In this example, the air cleaning devices A have a signal receiving portion that receives a control signal from the remote controller 52 and a control portion that, based on the received signal, turns an illuminator 32 on and off, turns the air cleaning devices A on and off, controls the amount of negative ions and ozone generated, and enables intermittent or timer-based generation.

Figure 28:
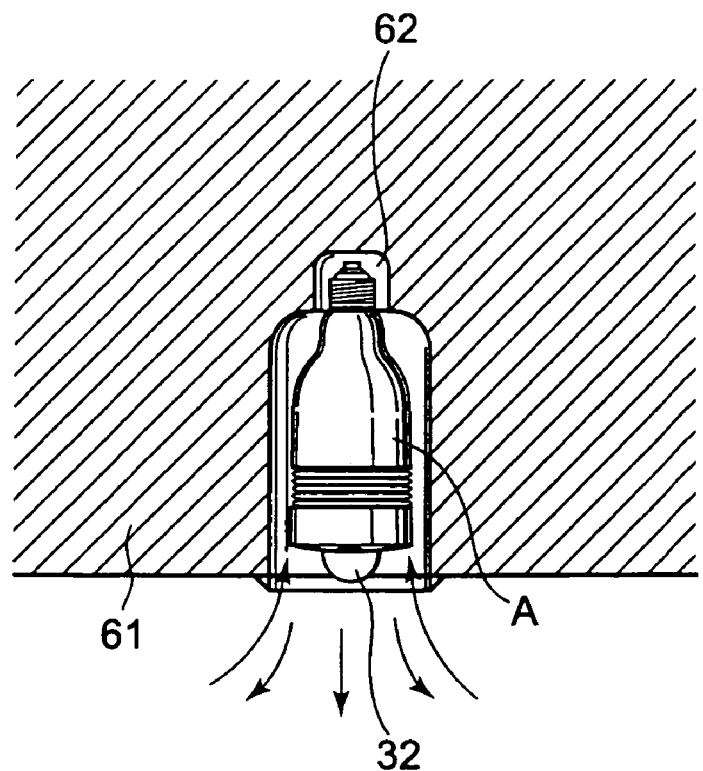
FIG. 28 is an explanatory view illustrating an air cleaning device according to this invention applied to a socket built in the ceiling.

FIG. 28 shows an example in which the air cleaning device A of this invention is attached to a socket 62 built in the ceiling 61. When a power switch is turned on, an illuminator 32 is lighted and, at the same time, a stream of air containing negative ions and ozone that is slightly heavier than air flows downward out of the ceiling 61 and is diffused.

Figure 29A:
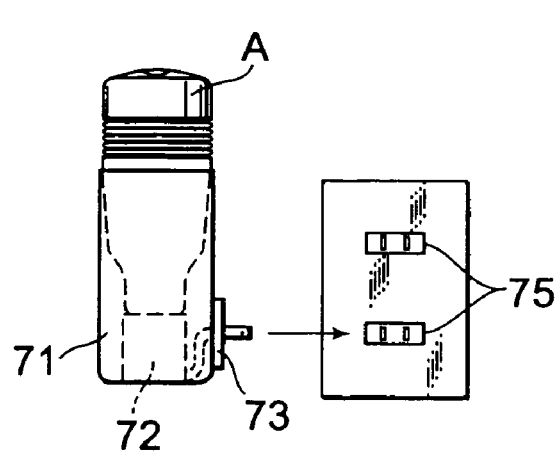
FIG. 29($a$) is an explanatory view illustrating an air cleaning device according to this invention accommodated in an attachment provided with a socket and a plug.
Figure 29B:
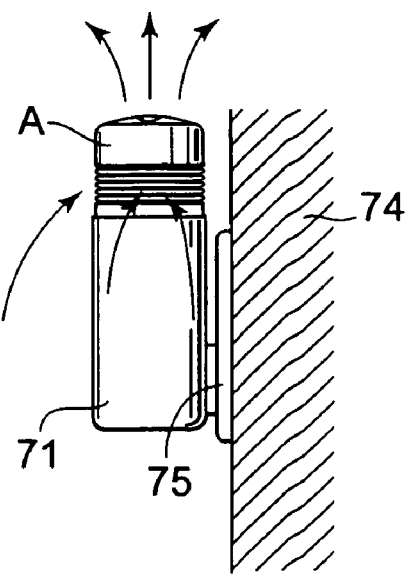

The air cleaning device A of this invention can be accommodated in an attachment 71 provided with a socket 72 and a plug 73, as shown in FIG. 29(a), and can be used by inserting the plug 72 into an electrical receptacle 75 formed in a wall 74 as shown in FIG. 29(b). By turning a switch on, a stream of air containing negative ions and ozone is released upward. Using the attachment in this manner with the plug inserted into the electrical receptacle formed in the wall enables the air cleaning device to be operated with ease even in the absence of a socket conforming to its base.

Figure 30:
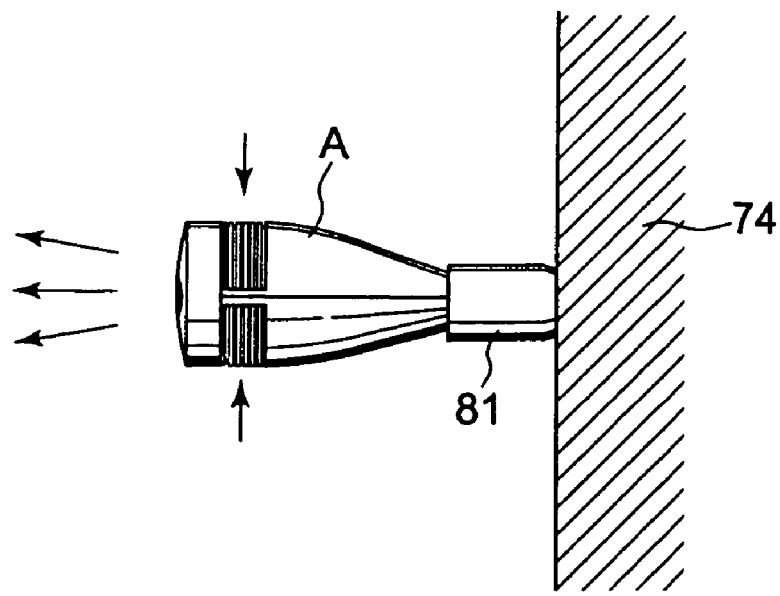
FIG. 30 is an explanatory view illustrating an air cleaning device according to this invention mounted in a socket attached to a wall.

FIG. 30 shows an example in which the air cleaning device A of this invention is mounted in a socket 81 attached to a wall 74. When a switch is turned on, a stream of air containing negative ions and ozone is released laterally.

Figure 31:
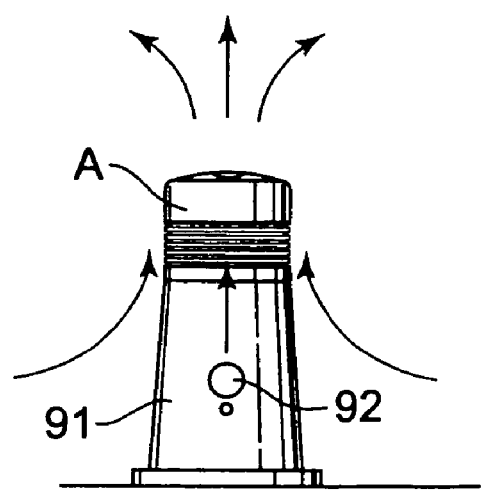
FIG. 31 is an explanatory view illustrating an air cleaning device according to this invention attached to a stand mounted on a table.

FIG. 31 shows an example in which the air cleaning device A of this invention is attached to a stand 91 mounted on a table equipped with an electrical receptacle and a power cord (neither shown). By turning a switch 92 on, a stream of air containing negative ions and ozone is released upward.

While the casing has been made from a synthetic resin material in any of the foregoing embodiments, it can be made from any other material, provided that if it is made from a material having conductivity, it is necessary to ensure insulation between itself and the conductive portions including the first electrode, second electrode, retainer, connectors, etc.

Though the shape of the casing in its plan view has been described as being circular, it may be any other shape, e.g., an oval shape or polygonal shape including a triangle, a tetragon, a pentagon, a hexagon, etc. Furthermore, while the foregoing description has shown a small-sized electric bulb as the contour of the casing, the contour may be that of a large-sized electric bulb or ball.

The lid has had the circular outlets. The outlets may be of any other shape. In addition, they are not necessarily be concentric accurately with the first electrode and the holes of the second electrode, but may be overlapped with the first electrode or with both the first electrode and the holes of the second electrode. Furthermore, it is selected whether the air cleaning device should have an illuminator, depending on its mounting locations.

When the air cleaning device is equipped with an illuminator, it is preferable that the illuminator is interlocked with the negative ion generator or ozone generator so that the illuminator can work during the operation of the negative ion generator or ozone generator and cannot do during the non-operation of the generator. As a result, the illuminator can also serve as display means showing the operation state of the generator.

In all the embodiments, the air cleaning device has been provided at its one end with a fed portion. However, the fed portion can be replaced with an attached portion having a similar configuration and, in addition, if the negative ion generator or ozone generator, power source, boosting transformer, etc. are incorporated in the air cleaning device, negative ions or both negative ions and ozone can be generated even where electricity is not fed.

The number of the first electrode used is four in the first, third and fourth embodiments, one in the second and fifth embodiments, and three in the sixth, seventh and eighth embodiments. Thus, at least one first electrode will suffice.

While the outlet or recess has been configured to have the cross pieces capable of preventing finger touch with the first electrode, such safety means can instead comprise a plurality of projections extending from the peripheral wall that defines the outlet or recess, or a combination of a concentric rib and support ribs projecting radially from the peripheral wall that defines the outlet or recess for supporting the concentric rib.

The AC/DC converter and the boosting transformer has been configured separately or integrally. Either configuration will do.

The portion for supplying air into the ozone generator has been formed on either the casing body or the lid. However, it may be formed on each of the two.

In the first embodiment, the casing body and the lid of the casing have been detachably attached to each other. However, since there is no electrode facing the first electrode, resulting in few possibility of dirtying the inside of the casing, as described earlier, the two may be made integral.

The second electrode has been detachably attached to the lid using the retainer in the third embodiment and using the connector in the fourth embodiment. However, it may be detachably attached to the lid using a screw and connected to the positive pole of the AC/DC converter or boosting transformer accommodated in the casing body using a connector.

Furthermore, while the second electrode has been described as being accommodated in the lid, it may be accommodated in the casing body.

The electric bulb has been shown as the illuminator. However, the illuminator can include a halogen lamp, a fluorescent lamp, a surface light-emitting element and a high-brightness light-emitting diode. A halogen lamp has the effect of securing a light projecting distance. A fluorescent lamp has the effect of securing high brightness while not accumulating heat. A surface light-emitting element has the effect of only requiring a small amount of power consumption, accumulating little heat and attaining a compact size due to its flat surface and no irregularities. A high-brightness light-emitting diode has the effect of only requiring a small amount of power consumption, accumulating little heat, ensuring its long service life and attaining a compact size.

In the mounting examples, the air cleaning devices equipped therein with the ozone generator have been cited. The mounting examples can be applied to the air cleaning devices equipped therein with the negative ion generator.

When the air cleaning device is attached to an untouchable position, e.g., the ceiling, the control portion having various control functions, e.g., a microcomputer, is disposed in the casing and a remote controller is used to interlock the negative ion generator or ozone generator and the illuminator or cause them to be operated separately, control the amount of negative ions and ozone generated with an increase or decrease in the number of electrodes to which voltage is applied, and enable intermittent or timer-based generation. Otherwise, a controller attached to a wall is used to enable the same operation and control.

Even when the air cleaning device is attached to a touchable location, the aforementioned remote controller or controller attached to the wall can be used to enable the same operation and control.

Furthermore, while the foregoing description relates to generation of either negative ions alone or both negative ions and ozone, ozone alone may be generated.

INDUSTRIAL APPLICABILITY

As has been described in the foregoing, in the air cleaning device according to the present invention, since a casing is bulb-shaped and is equipped with an attached or fed portion that is to be attached to an attaching or feed portion, attachment of the attached or fed portion to a socket for illumination enables negative ions and ozone to be released from above in a room or other such space, thereby making it possible to clean the air in the room or other such space and effect bactericidal and deodorant actions. In the case of the suspendible type of bulb-shaped casing, it is possible to provide a novel air cleaning device with various applications, as compared with conventional mount-type air cleaning devices disposed on the floor, a desk or other such flat place.

Furthermore, the negative ion generator can be constituted of first electrodes. In this case, therefore, there is few possibility of dirtying the inside of the casing, thus less requiring cleaning and washing operations of the inside of the casing and making the device maintenance easy.

In addition, since the casing is divided into the casing body and the lid which are attachable to and detachable from each other, after detaching the lid from the casing body it is possible to easily clean and wash the inside of the lid and, the second electrode exposed to dust and dirtied.

Moreover, since the second electrode is formed into a cylindrical one or a platelike one with circular holes and the first electrodes are formed into needle-like ones, it is possible to efficiently generate negative ions and ozone, stabilize the velocity of an air stream and increase the amount of the air stream. In the case of the air cleaning device with an embedded illuminator, it is possible to acquire the effects of negative ions and ozone even when the device is provided where illumination is required.

The invention claimed is:

1. An air cleaning device comprising:
a bulb-shaped casing provided at one end with a fed portion configured to be attached to a feed portion and connected to a commercial power source and at the other end with an outlet and with an illuminator socket;
an AC/DC converter accommodated in the casing for converting an alternating current from the fed portion into a direct current;
a boosting transformer accommodated in the casing for boosting voltage from the AC/DC converter; and
a negative ion generator projecting from a bottom in the outlet of the casing and connected to the boosting transformer for enabling application of high voltage from the boosting transformer to the negative ion generator to induce electrical discharge, generate negative ions, and release the negative ions from the outlet.

2. The air cleaning device according to claim 1, wherein the bulb-shaped casing comprises a casing body having one end provided with the fed portion and the other end being an open end, and a lid having one end provided with the outlet and the other end at least one of fixed and detachably attached to the open end of the casing body.

3. The air cleaning device according to claim 1, wherein the negative ion generator is a needle electrode having a distal end directed to a side of the outlet.

4. The air cleaning device according to claim 1, wherein the DC/AC converter and the boosting transformer are made integral.

5. The air cleaning device according to claim 1, wherein the bulb-shaped casing includes an illuminator at the other end.

6. The air cleaning device according to claim 1, wherein the fed portion comprises a base configured to be attached to and detached from a socket.

7. The air cleaning device according to claim 1, wherein the fed portion comprises a base having a pair of pins projecting from a peripheral surface in opposite directions.

8. The air cleaning device according to claim 1, wherein the fed portion comprises a plug having a pair of at least one of blades and pins configured to be attached to and detached from an electrical receptacle.

9. An air cleaning device comprising:
a bulb-shaped casing provided at one end with an attached portion configured to be attached to an attaching portion and connected to a commercial power source and at the other end with an outlet and a detachable illuminator; and
a negative ion generator accommodated in the casing for inducing electrical discharge and generating negative ions from the outlet.

* * * * *